United States Patent [19]

Huang et al.

[11] 4,154,762

[45] May 15, 1979

[54] OXIDATIVE DEHYDROGENATION OF ALCOHOLS TO ALDEHYDES AND KETONES

[75] Inventors: I-Der Huang, West Paterson; Leon M. Polinski, North Plainfield; Krishna K. Rao, Fairlawn, all of N.J.

[73] Assignee: Givaudan Corporation, Clifton, N.J.

[21] Appl. No.: 570,139

[22] Filed: Apr. 21, 1975

Related U.S. Application Data

[63] Continuation of Ser. No. 365,340, May 30, 1973, abandoned.

[51] Int. Cl.² .............................................. C07C 45/16
[52] U.S. Cl. .......................... 260/586 P; 260/590 R; 260/590 C; 260/590 D; 260/591; 260/592; 260/596; 260/598; 260/599; 260/603 R

[58] Field of Search ............... 260/586 P, 596, 590 R, 260/591, 592, 598, 599, 603 R, 590 C, 590 D

[56] References Cited

U.S. PATENT DOCUMENTS

| | | | |
|---|---|---|---|
| 3,156,735 | 11/1964 | Armstrong | 260/596 |
| 3,364,264 | 1/1968 | Hardman et al. | 260/586 P |
| 3,476,808 | 11/1969 | Etherington et al. | 260/586 P |
| 3,673,255 | 6/1972 | Etherington et al. | 260/586 P |

*Primary Examiner*—Norman Morgenstern
*Attorney, Agent, or Firm*—Thomas Cifelli, Jr.; Robert F. Tavares

[57] ABSTRACT

Monohydric primary or secondary saturated and unsaturated alcohols are oxidatively dehydrogenated to the corresponding aldehyde or ketone over a gold catalyst at temperatures between 280°–600° C. in the presence of oxygen.

27 Claims, No Drawings

OXIDATIVE DEHYDROGENATION OF ALCOHOLS TO ALDEHYDES AND KETONES

This is a continuation of application Ser. No. 365,340 filed May 30, 1973 now abandoned.

BACKGROUND OF THE INVENTION

1. Field of the Invention

This invention relates to a process for the vapor phase oxidative dehydrogenation of monohydric alcohols to form the corresponding aldehydes and ketones. More particularly, this invention relates to the oxidative dehydrogenation of alcohols to aldehydes and ketones using a gold catalyst.

2. The Prior Art

Aldehydes and ketones markedly influence the odor of many essential oils and the very satisfactory effects that can be achieved with these odoriferous compounds have long been known to perfumers.

Aldehydes and ketones exhibiting desirable olfactive properties include both those found in natural products such as essential oils and fruits of plants and those which are made synthetically. Examples of odoriferous aldehydes include n-valeraldehyde (occurring in musk, herbs), isovaleradldehyde (occurring in peppermint, clove, citronella Oils) n-hexenal (occurring in eucalyptus oils), α,β-hexenal or β-propyl acrolein (occurring in green vegetables), n-heptaldehyde (not naturally occurring), n-octyl aldehyde (occurring in lemon oil, lemongrass oil), n-nonyl aldehyde (occurring in mandarin, orris root, Ceylon cinnamon), n-capraldehyde (occurring in sweet orange, lemongrass, mandarin neroli, coriander), n-undecylaldehyde (not naturally occurring), n-dodecylaldehyde (occurring in oils of silver fir, lemon and rue), n-tridecylic aldehyde (not naturally occurring), n-tetradecyl aldehyde (occurring in ocotea, pinus, and Formosan camphor oils), n-hexadecanal, n-octadecanal, phenyl octaldehyde (occurring in neroli oil), benzaldehyde (occurring in rose, peach, apricot) and p-tert-butyl-alpha methyl hydrocinnamaldehyde (Lilial, trademark). Examples of odoriferous ketones include ionone (occurring in flower oil, violet moss, and costus root), methyl ionone (not naturally occurring), dibenzyl ketone (not naturally occurring), methyl nonyl ketone (occurring in rue oil), zingerone (occurring in oil of ginger), dehydrojasmone (not naturally occurring), menthone (occurring in peppermint, pennyroyal and geranium) and ethylamyl ketone (occurring in lavender oil).

These odoriferous aldehydes and ketones are so potent that when they occur naturally, they are frequently present in natural oils in fractions on the order of 1%, but are so strongly odoriferous that they markedly affect the character of a perfume or formulation to which they are incorporated. When prepared synthetically, the purity of the aldehydes or ketones is a controlling factor in their commercial use, as the presence of unpleasant by-odors resulting from by-products formed during the synthesis can make their use in perfume formulations totally unacceptable.

The art is continually seeking methods of preparing odoriferous aldehydes and ketones synthetically wherein the reaction product has reduced concentrations of objectionable by-products.

One method of preparing aldehydes which has attained fairly large scale and widespread use is the oxidative dehydrogenation of monohydric alcohols which involves mixing an oxygen-containing gas (such as air) with the alcohol and passing this mixture over or through a suitable catalyst.

The catalytic oxidative dehydrogenation reaction may be represented by the following equation:

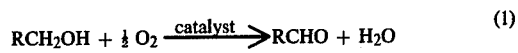

$$RCH_2OH + \tfrac{1}{2} O_2 \xrightarrow{\text{catalyst}} RCHO + H_2O \qquad (1)$$

where R represents branched and straight chain alkyl and alkenyl radicals having 1 to 16 carbon atoms, cycloalkyl and cycloalkenyl radicals having 5 to 16 carbon atoms, mononuclear and dinuclear aryl radicals and aralkyl radicals having 6 to 16 carbon atoms.

If the alcohol used in the catalytic oxidative dehydrogenation reaction is a secondary alcohol, the reaction product is a ketone in accordance with the following equation:

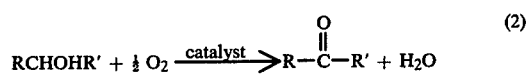

$$RCHOHR' + \tfrac{1}{2} O_2 \xrightarrow{\text{catalyst}} R-\overset{\overset{O}{\|}}{C}-R' + H_2O \qquad (2)$$

where R' is selected from the same group of radicals as R and may be the same or a different radical than R.

Copper and silver alone or in combination with each other or with another metal such as zinc or chrome, metal oxides such as zinc oxide, iron oxide, molybdenum oxide and rare earth oxides are used by the art as catalysts for the oxidative dehydrogenation of alcohols.

These catalysts are subject to certain disabilities such as short life and undesirable by-products which render their replacement by a more suitable catalyst highly desirable.

SUMMARY OF THE INVENTION

In accordance with the present invention, there is provided a process for the catalytic oxidative dehydrogenation of alcohols to produce aldehydes and ketones of high yield wherein the alcohol to be dehydrogenated is reacted in the presence of oxygen and a catalyst system containing gold as the sole component thereof.

As will be hereinafter illustrated, the use of a gold catalyst in the catalytic oxidative dehydrogenation of alcohols promotes the conversion of the alcohol to aldehydes and ketones at selectivities in the order of 80% to greater than 99% with minimum by-product formation.

The effectiveness of gold as a catalyst for the oxidative dehydrogenation of alcohols is quite surprising and unexpected as the use of gold alone does not promote other oxidations such as the oxidation of cumene. Thus N. H. A. Van Horn et al, reports in the Journal of Catalysis, 20 (408-423) 1971 at page 409, that gold is totally inactive by itself in promoting the cumene oxidation reaction.

Further, as will hereinafter be demonstrated, the use of a gold catalyst in the oxidative dehydrogenation of alcohols produces the corresponding aldehyde from the alcohol being dehydrogenated. Unlike the oxidative dehydrogenation of ketones, as disclosed in U.S. Pat. Nos. 3,476,808 and 3,673,255, the oxidative dehydrogenation of alcohols using a gold catalyst does not produce ethylenically unsaturated ketones from saturated ketones formed in the dehydrogenation of secondary alcohols or unsaturated aldehydes from saturated alcohols or additional unsaturation in alcohols partially unsaturated prior to oxidative dehydrogenation.

PREFERRED EMBODIMENTS

The present process is conveniently carried out by contacting a primary or secondary monohydric alcohol or mixtures thereof in the vapor phase together with molecular oxygen, such as air, in a suitable reactor containing the gold catalyst.

In effecting the oxidative dehydrogenation reaction, streams of the alcohol vapors and of the oxygen containing gas are mixed in proportions corresponding to about 0.10 to about 2.50 moles of free oxygen per mole of alcohol and preferably about 0.30 to about 1.50 moles of free oxygen per mole of alcohol and the vapor mixture is passed into contact with the metallic gold at a reaction temperature in the order of from 250° to 600° C. and preferably about 300° to 500° C.

The reaction is usually conducted at atmospheric pressure although with some alcohols, optimum oxidative dehydrogenation to aldehydes or ketones occurs at subatmospheric pressure.

Usually, the alcohol and oxygen vapors are passed first through a preheating zone where they are heated to approach the reaction temperature and then passed through or over the metallic gold catalyst. The gold is usually employed as a deposit on an inert support or in the form of a gold wire gauze or gold plated wire gauze. When a gold plated wire gauze is used as the catalytic medium, it is essential that at least the external surface of the gauze is plated with gold. It is preferred that a fine threaded mesh gauze having an individual thread diameter of 0.014 inches or less and generally a diameter of 0.002 to 0.003 inches be employed. Although the gauze may be woven entirely of gold thread, it is more economical and equally catalytically effective when the gold is plated on a wire gauze formed from a less expensive metal such as copper. When plated on a wire gauze such as copper wire gauze, it is preferred that the thickness of the gold plating be in the range of 20 to 50 microinches although plating thicknesses as low as 5 microinches will result in an effective catalyst medium.

The gold metal catalyst employed in the process of the present invention preferably has a low surface area and is generally less than 2.0 square meters per gram ($m^2/g$) and preferably less than 0.5 $m^2/g$.

Vapors flowing from the reaction zone are cooled to condense the organic products. The condensate consists for the most part of water, the unreacted alcohol and the corresponding aldehyde or ketone reaction product. The aldehyde or ketone is then recovered by any suitable method from the condensate, as by distillation, fractionation or extraction.

The gold catalyst of the present invention is effective in the oxidative dehydrogenation of alcohols over a wide range of alcohol and air mixtures and temperatures. Percent selectivity and percent conversion are high. As the terms are used herein, "percent selectivity" is 100 multiplied by the moles of aldehyde or ketone produced divided by the moles of alcohol converted and "percent conversion" is 100 multiplied by the moles of alcohol converted divided by the moles of alcohol in the feed.

The optimum reaction conditions for the oxidative dehydrogenation process of the present invention are dependent on the specific alcohol being dehydrogenated. For example, and as will hereinafter be more fully described, the optimum reaction conditions for the dehydrogenation of benzyl alcohol to benzaldehyde are a benzyl alcohol/air mixture of 40 mole percent benzyl alcohol-in-air, a feed rate of 30 grams/minute and a reaction temperature of 438°–497° C. When substantially the same reaction conditions are used for the oxidative dehydrogenation of closely related phenyl ethyl alcohol to phenyl acetaldehyde the conversion to the phenyl acetaldehyde is extremely low (e.g. 16.7% aldehyde) and optimum conversion to phenyl acetaldehyde is achieved (e.g. 35.1% aldehyde) at a phenyl ethyl alcohol/air mixture of 30 mole %, a feed rate of 5 grams/minute and a reaction temperature of 332°–370° C.

The following examples illustrate but do not limit the invention. Unless otherwise specified, all the reactions were conducted at atmospheric pressure.

EXAMPLE I

A catalyst tube reactor 25 inches long having a 1.07 inch inside diameter and fabricated from stainless steel was equipped at its inlet portion with an alcohol feed means, air feed means and separate alcohol and air preheat means. To the reactor outlet was connected a gas condensing and cooling means and a condensate collection means.

A gold plated wire gauze woven from 0.0067 inch diameter wire and weighing 285 grams was inserted in the reactor. The reactor was sealed and placed in a reactor furnace.

In a series of runs, 1-decanol was pumped into the alcohol feed means at varying feed rates. The decanol was preheated to 275° C. and the alcohol vapors were contacted with air at 25° C. flowing into the reactor at varying rates. The mixture of vaporized decanol and air entered the reactor and was reacted therein in the presence of the gold plated gauze at varying furnace temperatures. The gaseous reaction product issued from the reactor was condensed, cooled and collected.

A material balance was made on the reaction system. The condensate consisted of organic material and water. The organic material was separated from the water and analyzed by vapor phase chromatography. The results of the series of dehydrogenation runs are summarized in Table I below.

TABLE I

| | Dehydrogenation of Decanol to Decanal | | | | | | |
|---|---|---|---|---|---|---|---|
| Run No. | Decanol feed rate (gm/min) | Air flow rate cc/min | Reactor (Hot Spot) Temp. °C. | Condensate Analysis | | | Material Balance (gms reaction product/grams decanol fed to reactor) |
| | | | | Decanal % | Decanol % | Lights % | |
| 1 | 4.00 | 1500 | 410° C. | 54.27 | 45.1 | 0.0 | 104/100 |
| 2 | 4.03 | 2200 | 415° C. | 31.30 | 66.8 | 2.0 | 102.8/100 |
| 3 | 2.35 | 750* | 400° C. | 43.60 | 55.3 | 1.1 | 106.1/100 |

*Air preheated to 225° C.

EXAMPLE II

The procedure of Example I was repeated with the exception that 4.0 grams/minute 1-dodecanol (lauric alcohol) heated to a temperature of 275° C. was passed to the reactor mixed with an air feed of 1,500 cc/minute at 270° C. and heated in the reactor at 400° C.

Analysis of the organic portion of the reaction product condensate by vapor phase chromatography indicated a 41.8% conversion to 1-dodecanal with no by-product formation.

EXAMPLE III

A five tube reactor was constructed and equipped at its inlet portion with separate alcohol and air feed means, separate alcohol and air preheat means and connected at its outlet portion to a gas product condensing means, a cooling means and collecting means. Each tube of the reactor was 33.5 inches long having an 0.87 inch inside diameter and fabricated from 316 stainless steel. In each tube was inserted a gold plated wire gauze woven from 0.0067 inch diameter thread which weighted 190 grams. The multi-tube reactor was placed in a furnace heated at 340° C. n-Octanol was pumped into the alcohol feed means at the rate of 30 grams/minute. The n-octanol was preheated, vaporized and mixed with preheated air in such a manner that a 20 mole % n-octanol-in-air mixture heated to 300° C. entered the reactor to be oxidized therein in the presence of the gold plated gauze catalyst at 340° C. The gaseous reaction product that issued from the reactor was condensed, cooled and collected.

Analysis of the organic layer of the reaction product condensate issued from the multi-tube reactor indicated that the conversion of n-octanol to octanol in a single pass through the reactor was 90.5% and the selectivity was 91.5%. The gold catalyst maintained its activity and its selectivity after 1900 hours of use.

Vapor phase chromatographic analysis of the organic portion of the reaction product condensate indicated that it consisted of 82.7% octanal, 9.5% n-octanol and 7.8% light by-products.

For purposes of contrast, the dehydrogenation of n-octanol was attempted with a Cu—ZnO—$Bi_2O_3$ catalyst. The catalyst was prepared and conditioned by impregnating the mixed oxide catalyst over a low surface area brass catalyst carrier, reduced with $H_2$, reoxidized and rereduced with $H_2$ until no exothermic reaction was noted. 775 grams of conditioned catalyst on 30 pounds of inert support was added to a 3" (O.D.)×43" long inconel reactor filling 36" of the length of the reactor.

n-Octanol was pumped at 50 lbs./hr. through the inconel reactor held at 470° C. over the first ⅔ of its length and at 400° C. over the last ⅓ of the packed catalyst system.

The conversion of octanol reached a maximum of 88.6% while the selectivity toward octanal reached a maximum of 79.8% and slowly declined to 72% as the reaction proceeded. It was necessary to replace the catalyst after 600–700 hours of use.

EXAMPLE IV

The procedure of Example III was repeated with the exception that n-heptanol was substituted for n-octanol.

Analysis of the reaction product issued from the multi-tube reactor indicated that the conversion of n-heptanol to heptanal in a single pass through the reactor was 53.7%, and the selectivity was 88%.

Vapor phase chromatographic analysis of the reaction product indicated that it consisted of 47.3% heptanal, 46.3% heptanol and 6.4% light by-products (on a water-free basis).

EXAMPLE V

The procedure of Example IV was repeated with the exception that the heptanol/air mixture was fed to the reactor maintained under vacuum, the total system pressure being 250 mm Hg.

Vapor phase chromatograhic analysis of the organic layer of the reaction product condensate indicated that it consisted of 70.2% heptaldehyde, 23.8% heptanol and 6.0% by-product. The conversion was found to have increased to 70.2% and selectivity was 92%.

EXAMPLE VI

The procedure of Example III was repeated with the exception that n-hexanol was substituted for n-octanol and the following reaction conditions were employed:
Feed rate of n-hexanol to reactor: 15 gm./min.
n-Hexanol/air mixture: 15 mole % hexanol-in-air
Reactor bed temperature: 320° C.

The conversion of n-hexanol to hexanal was found to be 52.6%. The selectivity was calculated to be 90.0%.

Vapor phase chromatographic analysis of the organic layer of the reaction product condensate indicated that it consisted of 47.3% hexanal, 47.4% n-hexanol and 5.3% lights.

EXAMPLE VII

The procedure of Example III was repeated with the exception that n-butanol was substituted for n-octanol and the following reaction conditions were employed:
Feed rate of n-butanol to reactor: 15 gm./min.
n-butanol/air mixture: 40 mole % butanol-in-air
Furnace temperature: 320° C.
Reaction (hot spot) temperature: 443° C.

The selectivity of butanol to butyraldehyde was calculated to be 95%.

Vapor phase chromatographic analysis of the organic layer of the reaction product condensate indicated that it consisted of 42.9% butyraldehyde, 55% butanol and 2.1% other by-products.

EXAMPLE VIII

The procedure of Example III was repeated with the exception that benzyl alcohol was substituted for n-octanol and a series of dehydrogenation runs were conducted to determine the optimum conditions for the oxidative dehydrogenation reaction. The results of this series of oxidative dehydrogenation runs are summarized in Table II below. Analysis of the organic layer of the condensate obtained from the reactor outlet was by vapor phase chromatography.

TABLE II

Dehydrogenation of Benzyl Alcohol to Benzaldehyde

| Run No. | Feed Rate gm/min | Mole % Alc.-in-air | Range of Inside Temps. near hot spot | Condensate Analysis | | |
|---|---|---|---|---|---|---|
| | | | | % Aldehyde | % Alcohol | % Other |
| *1 | 30 | 40 | 438°–497° C. | 53.3 | 44.8 | 1.9** |
| 2 | 30 | 25 | 440°–502° C. | 43.9 | 48.8 | 7.3 |
| 3 | 20 | 40 | 360°–460° C. | 43.3 | 55.0 | 1.7 |
| 4 | 20 | 25 | 344°–455° C. | 31.3 | 57.9 | 10.8 |
| 5 | 40 | 40 | 549°–652° C. | 45.2 | 52.0 | 2.8 |

*The pH of the crude reaction product was determined to range between 5–6 indicating that very little benzoic acid had formed.
**The selectivity to benzaldehyde was 96.5%.

Table II indicates that the optimum conditions for the dehydrogenation of benzyl alcohol are a benzyl alcohol/air mixture of 40 mole % alcohol in air, a feed rate of 30 grms/min and a reaction temperature of 438°–497° C. (Run No. 1).

EXAMPLE IX

The procedure of Example III was repeated with the exception that myristic alcohol [$CH_3(CH_2)_{12}CH_2OH$] was substituted for n-octanol and a series of oxidative dehydrogenation runs were conducted to determine the optimum conditions for the oxidative dehydrogenation reaction. The results of this series of oxidative dehydrogenation runs is summarized in Table III below. Analysis of the organic layer of the condensate obtained from the reactor outlet was by vapor phase chromatography.

TABLE III

Dehydrogenation of Myristic Alcohol to Myristic Aldehyde

| Run No. | Mole % in air | Feed Rate gm/min | Furnace Temp. °C. | Condensate Analysis | | | Conversion |
|---|---|---|---|---|---|---|---|
| | | | | Aldehyde | Alcohol | (Heav./lts.) | |
| 1 | 8 | 3 | 349 | 15.0 | 56.6 | 5.8/22.6 | 43.4 |
| 2 | 10 | 10 | 320 | 36.3 | 50.4 | 5.7/7.6 | 49.6 |
| 3 | 16 | 20 | 312 | 8.2 | 84.7 | 6.4/0.7 | 15.3 |
| 4 | 13 | 20 | 312 | 57.4 | 33.0 | 3.0/6.6 | 67 |
| 5 | 10 | 20 | 312 | 10.7 | 83.6 | 5.2/0.5 | 16.4 |
| 6 | 30 | 30 | 330 | 5.6 | 85.7 | 6.6/2.1 | 14.3 |
| 7 | 25 | 30 | 330 | 11.7 | 80.2 | 3.2/5.0 | 19.8 |
| 8 | 20 | 30 | 330 | 26.0 | 58.0 | 5.6/10.4 | 42 |
| 9 | 15 | 30 | 330 | 39.5 | 46.1 | 2.6/11.8 | 53.9 |
| *10 | 13 | 20 | 312 | 59.2 | 29.9 | 3.5/7.4 | 70.1 |

*Repeat of run 4 to establish reproducibility

Table III indicates that the optimum conditions for the oxidative dehydrogenation of myristic alcohol are myristic alcohol/air mixture of 13 mole % alcohol in air, a feed rate of 20 grms/min. and a furnace temperature of 312° C. (run Nos. 4 and 10).

EXAMPLE X

A single tube reactor was constructed and equipped at its inlet portion with an alcohol and an air feed means, separate alcohol and air preheat means and connected at its outlet portion to a gas product condensing means, a cooling means and a collection means. The reactor tube was 33.5 inches long having a 0.87 inch diameter and fabricated from stainless steel. To the tube was inserted a gold plated wire gauze woven from 0.0067 inch diameter thread which weighed 190 grams. The reactor was divided into 3 sequential temperature zones respectively of 340° C., 300° C. and 280° C., each zone being 11 inches long. In a series of runs, phenyl ethyl alcohol (PEA) was pumped into the alcohol feed means at varying feed rates. The PEA was preheated, vaporized and mixed with varying amounts of preheated air and the alcohol/air mixture was delivered to the reactor.

The results of this series of dehydrogenation runs is summarized in Table IV below. Analysis of the organic layer of the condensate obtained from the reactor outlet was by vapor phase chromatography.

TABLE IV

Dehydrogenation of Phenyl Ethyl Alcohol to Phenyl Acetaldehyde

| Run No. | Mol % in Air | Feed Rate gm/min. | Reaction Temp Range | Unconv. PEA % | Aldehyde | Others |
|---|---|---|---|---|---|---|
| 1 | 40 | 30 | 453°–549° C. | 79.5 | 16.7 | 3.8 |
| 2 | 40 | 15 | 406°–426° C. | 77.4 | 20.9 | 1.7 |
| 3 | 25 | 15 | 454°–544° C. | 70.3 | 13.2 | 16.5 |
| 4 | 40 | 10 | 361°–375° C. | 74.3 | 23.4 | 1.7 |
| 5 | 40 | 5 | 301°–311° C. | 73.4 | 23.9 | 2.7 |
| 6 | 30 | 5 | 332°–370° C. | 61.2 | 35.1 | 3.7 |

Table IV indicates that the optimum conditions for the dehydrogenation of PEA are PEA alcohol/air mixture of 30 mole % alcohol in air, a feed rate of 5 grms/minute and a reaction temperature of 332°–370° C.

EXAMPLE XI

To a catalyst tube reactor 5 inches long having a 0.56 inch inside diameter fabricated from copper equipped at its outlet portion with separate alcohol feed means, air feed means, separate alcohol and air preheat means and connected at its outlet portion to a gas condensing means, and a cooling and collection means, was inserted a gold plated wire gauze woven from 0.003 inch diameter thread and weighing 32 grams. The copper tube reactor was placed in a furnace heated at 350° C. p-Tertiary butyl alpha methyl hydrocinnamic alcohol (BMHCA) was pumped into the alcohol feed means at the rate of 1.0 gram/minute. The BMHCA was preheated, vaporized and mixed with preheated air in such a manner that a 30 mole % alcohol in air mixture entered the reactor to be oxidized therein in the presence of the gold plated gauze catalyst.

Vapor phase chromatographic analysis of the organic layer of the reaction product condensate collected from the reactor indicated that it consisted of 37.5% p-t-butyl alpha methyl hydrocinnamaldehyde, 53.5% BMHCA and 9% by-product. Selectivity toward p-t-butyl alpha methyl hydrocinnamaldehyde was 80.8%.

EXAMPLE XII

The procedure of Example XI was repeated with the exception that undecylenic alcohol [$CH_2=CH(CH_2)_8CH_2OH$] was substituted for the BMHCA and the following reaction conditions were used:

Feed rate of undecylenic alcohol to reactor: 1.0 gm/min.
Undecylenic alcohol/air mixture: 20 mole % alcohol-in-air
Furnace temperature: 370° C.

The reaction was conducted at near atmospheric pressure. The product was analyzed to be 32.4% undecylenic aldehyde and 67.6% unconverted alcohol.

No by-products were observed in the reaction product condensate removed from the reactor, apparent selectivity to aldehyde being 100%.

EXAMPLE XIII

The procedure of Example XI was repeated with the exception that hexahydrobenzyl alcohol (HBA) was substituted for the BMHCA and the following reaction conditions were used:

Feed rate of HBA to reactor: 1 gm/min.
HBA/air mixture: 20 mole % alcohol in air
Furnace temperature: 540° C.
Reaction temperature: 370°–430° C.

Vapor phase chromatographic analysis of the organic layer of the reaction product condensate indicated that it consisted of 49.7% hexahydrobenzaldehyde, 43.3% HBA and 7% unidentified by-products. Analysis of the condensate by oximation indicated 53.8% aldehyde. The conversion was 57% while the selectivity toward the aldehyde was 87.8%.

EXAMPLE XIV

The procedure of Example XI was repeated with the exception that 2,6 dimethyl octanol-8 (DMO) was substituted for the BMHCA and the following reaction conditions were used:

Feed rate of DMO to reactor: 1.5 gm/min.
DMO/air mixture: 21 mole % alcohol in air
Furnace temperature: 430° C.
Reaction (hot spot) temperature: 450° C.

Vapor phase chromatographic analysis of the organic layer of the reaction product condensate indicated that it consisted of 76.3% dimethyl octanal, 10.4% DMO, 16.3% geraniol, 4.1% volatile matter and the remainder heavy by-products. Conversion was 89.6% with selectivity to DMO (on a geraniol free basis) being 90%.

EXAMPLE XV

The procedure of Example XI was repeated with the exception that an alcohol mixture consisting of ortho, para, and meta cuminyl alcohol was substituted for the BMHCA and the following reaction conditions were used:

Feed rate of cuminyl alcohol to reactor: 2.55 gms/min.
Cuminyl alcohol/air mixture: 52% (volume) alcohol in air
Furnace temperature: 440°–480° C.
Reaction (hot spot) temperature: 400°–425° C.

The reaction was conducted for 50 minutes and 124.5 grams of an organic alyer was separated from the condensate collected from the reactor.

Vapor phase chromatographic analysis of the organic layer of the reaction product condensate indicated that it consisted of 66.17% cuminic aldehyde and 33.82% cuminyl alcohol. No lights were detected. The crude organic layer (124.5 gms.) was distilled in a Vigreaux column.

The product obtained consisted of 84.03 grams cuminic aldehyde, 37.76 grams cuminyl alcohol and 2.7 grams residue. The cuminyl alcohol fed to the reactor was 89.74 gms indicating a 93.63% yield on the alcohol converted. Conversion was calculated to be 70.38%.

EXAMPLE XVI

The procedure of Example XI was repeated with the exception that secondary butanol [$CH_3-CHOH-CH_2-CH_3$] was substituted for the BMHCA and the following reaction conditions were used:

Feed rate of sec.-butanol to reactor: 1.1 gm/min
Sec.-butanol/air mixture: 20 mole % alcohol in air
Reaction (hot spot) temperature: 595° C.
Furnace temperature: 450° C.

Vapor phase chromatographic analysis of the organic portion of the reaction product condensate indicated that it consisted of 71.5% methyl ethyl ketone 24.4% secondary butanol, 3.7% by-product and 0.4% lights. Conversion was over 75% and selectivity to methyl ethyl ketone was over 93%.

EXAMPLE XVII

The procedure of Example XI was repeated with the exception that para isopropyl cyclohexanol (PIC) was substituted for the BMHCA and the following reaction conditions were used:

Feed rate PIC to reactor: 1.42 gms/min.
PIC/air mixture: 26.8 mole % alcohol-in-air
Furnace temperature: 430°–450° C.
Reaction bed temperature: 445°–465° C.

Vapor phase chromatographic analysis of the organic portion of the reaction product condensate indicated that it consisted of 62.7% para isopropyl cyclohexanone, 34.9% PIC and 2.4% lights. No ethylenically unsaturated ketone by-product was detected in the analysis. Selectivity towards para isopropyl cyclohexanone was over 96%.

EXAMPLE XVIII

The procedure of Example XI was repeated with the exception that 2-octanol was substituted for the BMHCA and the following reaction conditions were used:
  Feed rate 2-octanol to reactor: 1.0 gm/min
  2-octanol/air mixture: 20 mole % alcohol in air
  Furnace temperature: 480°-500° C.
  Reactor bed temperature: 520°-540° C.
  Vapor phase chromatographic analysis of the organic layer separated from the reaction product condensate indicated that it consisted of 73.9% methyl hexyl ketone, 23.6% 2-octanol and 1.6% light by-products. Selectivity to ketone was greater than 97% while conversion was over 75%.

EXAMPLE XIX

The procedure of Example XI was repeated with the exception that cis-3-hexen-1-ol (leaf alcohol) a rather labile alcohol was substituted for the BMHCA and the following reaction conditions were employed:
  Feed rate cis-3-hexen-1-ol to reactor: 1.5 gms/min
  cis-3-hexen-1-ol/air mixture: 20 mole % alcohol in air
  Furnace temperature: 440° C.
  Reactor bed temperature: 430° C.
  Vapor phase chromatographic analysis of the organic layer of the condensate obtained from the reactor outlet indicated that it consisted of 61.3% aldehydes (including cis-3-hexanal), 30.3% cis-3-hexen-1-ol and 8.4% light by-products. Selectivity to aldehydes was 88%.

What is claimed is:

1. A process for producing aldehydes and ketones of the formula:

from the corresponding monohydric alcohol of the formula

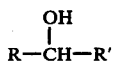

without at the same time producing carbon-carbon double bonds from carbon-carbon single bonds
wherein:
  R is selected from the group consisting of those branched and straight chain alkyl and alkenyl radicals of 2 to 16 carbon atoms, cycloalkyl and cycloalkenyl radicals of 5 to 16 carbon atoms and mononuclear and dinuclear aralkyl radicals of 6 to 16 carbon atoms which have two tetrasubstituted carbon atoms C$\alpha$ and C$\beta$ each of which has at least one hydrogen atom substituent and which are bonded with respect to the alcohol group in the manner

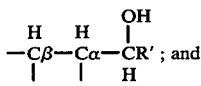

R' is selected from the group consisting of hydrogen, branched and straight chain alkyl and alkenyl radicals of 1 to 16 carbon atoms, cycloalkyl and cycloalkenyl radicals of 5 to 16 carbon atoms, mononuclear and dinuclear aryl radicals and aralkyl radicals of 6 to 16 carbon atoms; which comprises contacting the monohydric alcohol in the vapor phase with an oxygen containing gas at a temperature of between 250° to 600° C. in the presence of a catalyst consisting of gold.

2. The process of claim 1 wherein the monohydric alcohol has the general formula:

3. The process of claim 1 wherein the monohydric alcohol has the general formula:

and R' is not hydrogen.

4. The process of claim 1 wherein the oxygen containing gas is air.

5. The process of claim 1 wherein the vapors of monohydric alcohol and the oxygen containing gas are mixed in proportions of about 0.10 to about 2.50 moles of oxygen per mole of alcohol.

6. The process of claim 1 wherein the monohydric alcohol is contacted with the oxygen containing gas at atmospheric pressure.

7. The process of claim 1 wherein the monohydric alcohol is contacted with the oxygen containing gas at subatmospheric pressure.

8. The process of claim 1 wherein the gold catalyst is a wire gauze plated with a gold deposit having a surface area of 2.0 square meters per gram or less.

9. The process of claim 8 wherein the wire in the gauze catalyst has a diameter of 0.014 inch or less and the gold plating deposited thereon has a thickness ranging from about 5 to about 50 microinches.

10. The process of claim 1 wherein the gold catalyst is a pure gold wire gauze having a surface area of 2.0 square meters per gram or less.

11. The process of claim 1 wherein the gold catalyst is an inert support plated with a gold deposit having a surface area of 2.0 square meters per gram or less.

12. The process of claim 11 wherein the gold plating deposited on the inert support has a thickness ranging from about 5 to about 50 microinches.

13. The process of claim 2 wherein the alcohol is 1-decanol.

14. The process of claim 2 wherein the alcohol is 1-dodecanol.

15. The process of claim 2 wherein the alcohol is n-octanol.

16. The process of claim 2 wherein the alcohol is n-heptanol.

17. The process of claim 2 wherein the alcohol is n-hexanol.

18. The process of claim 2 wherein the alcohol is n-butanol.

19. The process of claim 2 wherein the alcohol is myristic alcohol.

20. The process of claim 2 wherein the alcohol is p-tertiary butyl alpha methyl hydrocinnamic alcohol.

21. The process of claim 2 wherein the alcohol is undecylenic alcohol.

22. The process of claim 2 wherein the alcohol is hexahydrobenzyl alcohol.

23. The process of claim 2 wherein the alcohol is 2,6-dimethyl octanol-8.

24. The process of claim 2 wherein the alcohol is cuminyl alcohol.

25. The process of claim 3 wherein the alcohol is secondary butanol.

26. The process of claim 3 wherein the alcohol is p-isopropyl cyclohexanol.

27. The process of claim 3 wherein the alcohol is 2-octanol.

* * * * *